United States Patent [19]

Sioma et al.

[11] Patent Number: 5,303,029
[45] Date of Patent: Apr. 12, 1994

[54] SAMPLE EVALUATION BY DUST MEASURING

[75] Inventors: Edward M. Sioma, Levittown; James Litterio, Bensalem; Wen H. Chia, Ambler, all of Pa.

[73] Assignee: Rohm and Haas Company, Philadelphia, Pa.

[21] Appl. No.: 903,383

[22] Filed: Jun. 24, 1992

[51] Int. Cl.⁵ .............................. G01N 21/53
[52] U.S. Cl. .................................. 356/339
[58] Field of Search ................... 356/339, 439

[56] References Cited

U.S. PATENT DOCUMENTS

| | | | |
|---|---|---|---|
| 2,822,719 | 2/1958 | Fike | 356/438 |
| 4,839,529 | 6/1989 | Fruengel | 356/339 |
| 4,993,838 | 2/1991 | Tresouthick et al. | 356/439 |

OTHER PUBLICATIONS

Lorenz Mebatebau Brochure, SP2 Machine, "Sedimentation Measuring Instrument of Assessing the Absence of Dust in Powders and Granules", no date.

*Primary Examiner*—Richard A. Rosenberger
*Attorney, Agent, or Firm*—Terence P. Strobaugh; Clark R. Carpenter

[57] ABSTRACT

A tubular test chamber of square cross-section minimizes reflection of stray light from the interior surface of the test chamber onto the detector during measurement by an optical system which is based upon right angle light scattering by the dust particles of a test sample. A rotary solenoid is utilized to open a trap door through which a sample is dropped into the test chamber during energization so that the internal spring of the solenoid can be used to bias the door closed upon deenergization thereof. The electronic circuitry which supports the measurement process provides an output in the form of a single "characteristic number" for each sample measured and has a novel feedback circuit used in auto-zeroing of the device.

6 Claims, 8 Drawing Sheets

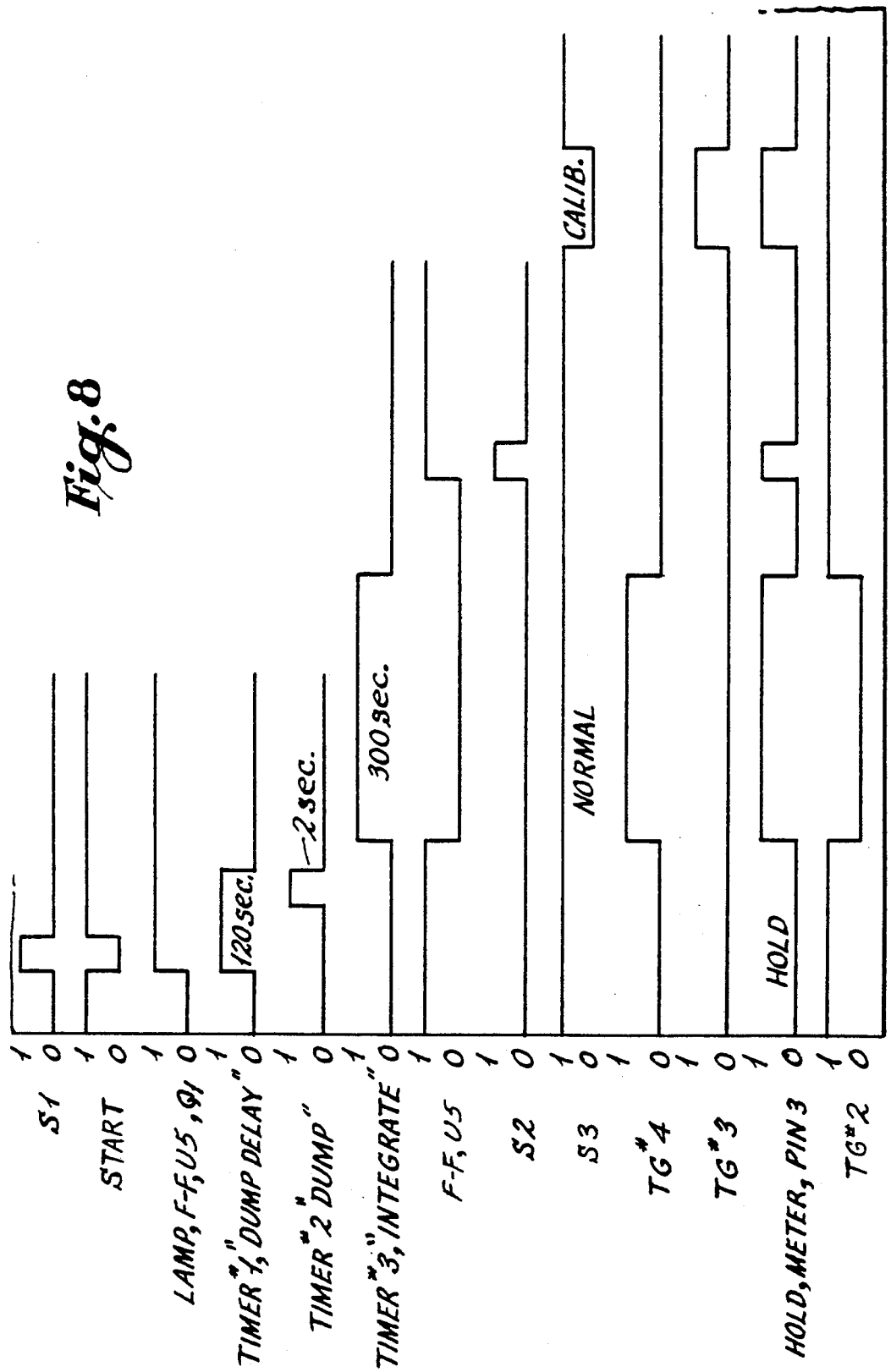

5,303,029

SAMPLE EVALUATION BY DUST MEASURING

PRIOR ART CROSS REFERENCES

The following reference is exemplary of the prior art and the disclosure thereof is incorporated, by reference, into the instant application.

Lorenz Meßätebau Brochure, SP2 Machine, "Sedimentation Measuring Instrument for Assessing the Absence of Dust in Powders and Granules", no date.

BACKGROUND OF THE INVENTION

The invention is in the field of measurement of the dustiness of samples of dry flowable (DF) substances. More particularly, the invention utilizes an optical apparatus to measure light reflected from dust particles in order to quantify dustiness of dry flowable substances such as pesticide formulations.

Exemplary of the prior art in this field is the above-referenced Lorenz publication which discloses use of an optical system having a stainless steel tube of circular cross-section into which a sample is dropped for measurement of the absorption of light by the sample. A digital processor is utilized to monitor and control the process of measurement and recording thereof. The record of the sedimentation process is provided by a plotter at the end of each measurement so that the spectrum thereof can be used as fingerprint for assessing the quality of the measured substance. The record contains the date, time, sample identification number, diagram of sedimentation spectrum, the instantaneous value of the dust, and the assessment.

It is desirous to simplify the measurement apparatus both mechanically and electrically and provide a simpler, yet more versatile and reliable testing chamber, associated optics system, and supporting electronics so as to obtain: (i) more precise measurement by minimizing extraneous reflections from the inner surface of the test chamber, (ii) a simple mechanical adjustment of the apparatus when the particle sizes vary from sample to sample, (iii) quick and easy calibration of the device, (iv) reliable, less expensive control of the trap door by which the sample is dumped into the test chamber, and (v) a simple means for comparing samples which does not require complex calculations and use of a recording device.

Thus, it is an object of the instant invention to utilize reflection of light from the material being evaluated, rather than absorption of the light by the material, in order that the measurement increases directly in proportion to the material and light reflected therefrom.

Additionally, it is an object of the invention to provide for vertical adjustability of the optics portion of the device in order to obtain proper measurement of a substance according to particle size of the sample under test.

Also, it is an object of the invention to provide for simple, rapid, precise, and repeatable calibration of the photodetector in preparation for each evaluation.

Further, it is an object of the invention to simplify the overall control process by utilizing a rotary solenoid which, when energized, provides the motive force for opening the trap door of the sample cup from which the substance being evaluated is dropped into the test chamber and, when deenergized, provides a force sufficient for light-tight closing of the trap door by means of the internal spring of the rotary solenoid.

Still further, it is an object of the invention to provide an integrated output in the form of a single "characteristic number" for each sample that is tested, in order that many samples may be compared easily and rapidly without requiring complex calculations or an expensive recording device.

These and other objects of the invention will become apparent from the following disclosure.

SUMMARY OF THE INVENTION

The invention incorporates an optical system which is based upon right angle light scattering by the dust particles of a sample of the substance. This "reflection" technique results in no reading when no dust is present, whereas the totally opposite "absorption" technique of the Lorenz device results in a maximum reading when no dust is present. The invention utilizes a tubular test chamber of square cross-section so as to minimize reflection of stray light from the interior surface of the test chamber onto the detector during the measurement. Additionally, a rotary solenoid is used to close, as well as open, the trap door through which a sample is dropped into the test chamber. The rotary solenoid opens the door during energization, and the internal spring of the solenoid biases the door closed upon deenergization thereof.

The electronic circuitry which supports the measurement process provides an output in the form of a single "characteristic number" for each sample measured, thus obviating the need for an expensive recording device and simplifying and speeding the comparison between many samples without the need for complex calculations being performed on this output in order to make such a comparison.

BRIEF DESCRIPTION OF THE DRAWINGS

FIG. 4b is a block diagram of the disclosure of FIG. 4a.

FIG. 8 is a timing diagram for the invention.

DETAILED DESCRIPTION OF THE INVENTION

Figure 1:
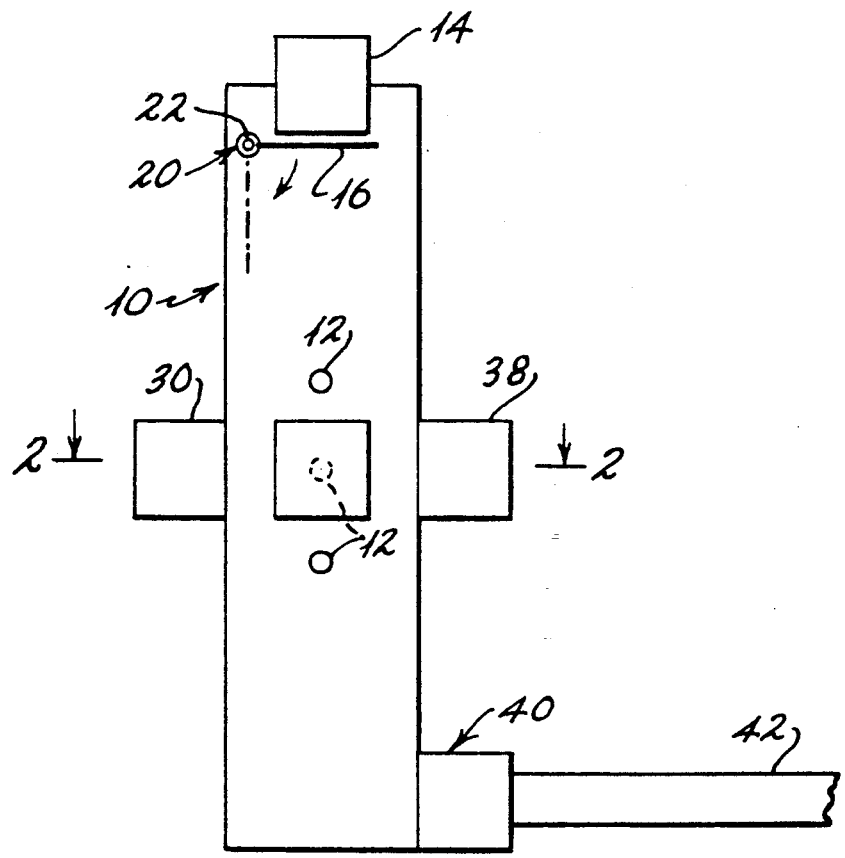
FIG. 1 is an elevational view of apparatus of the invention.
Figure 2:
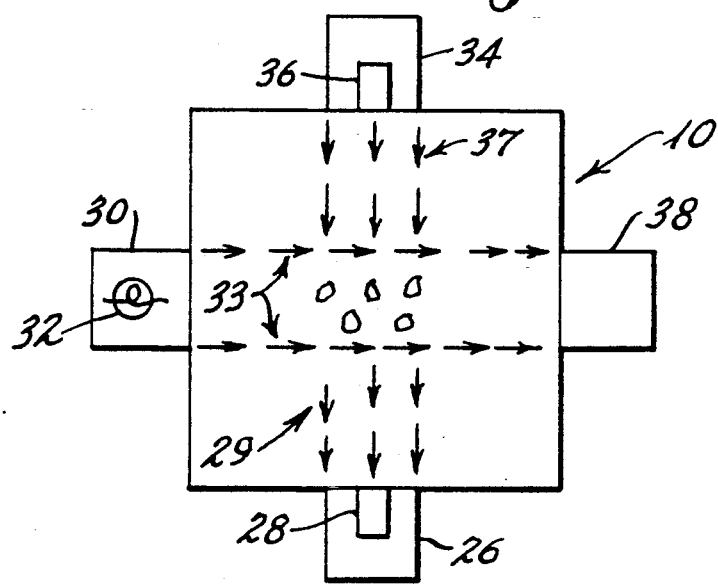
FIG. 2 is a cross-section as viewed generally in the direction of arrows 2—2 of FIG. 1.
Figure 3:
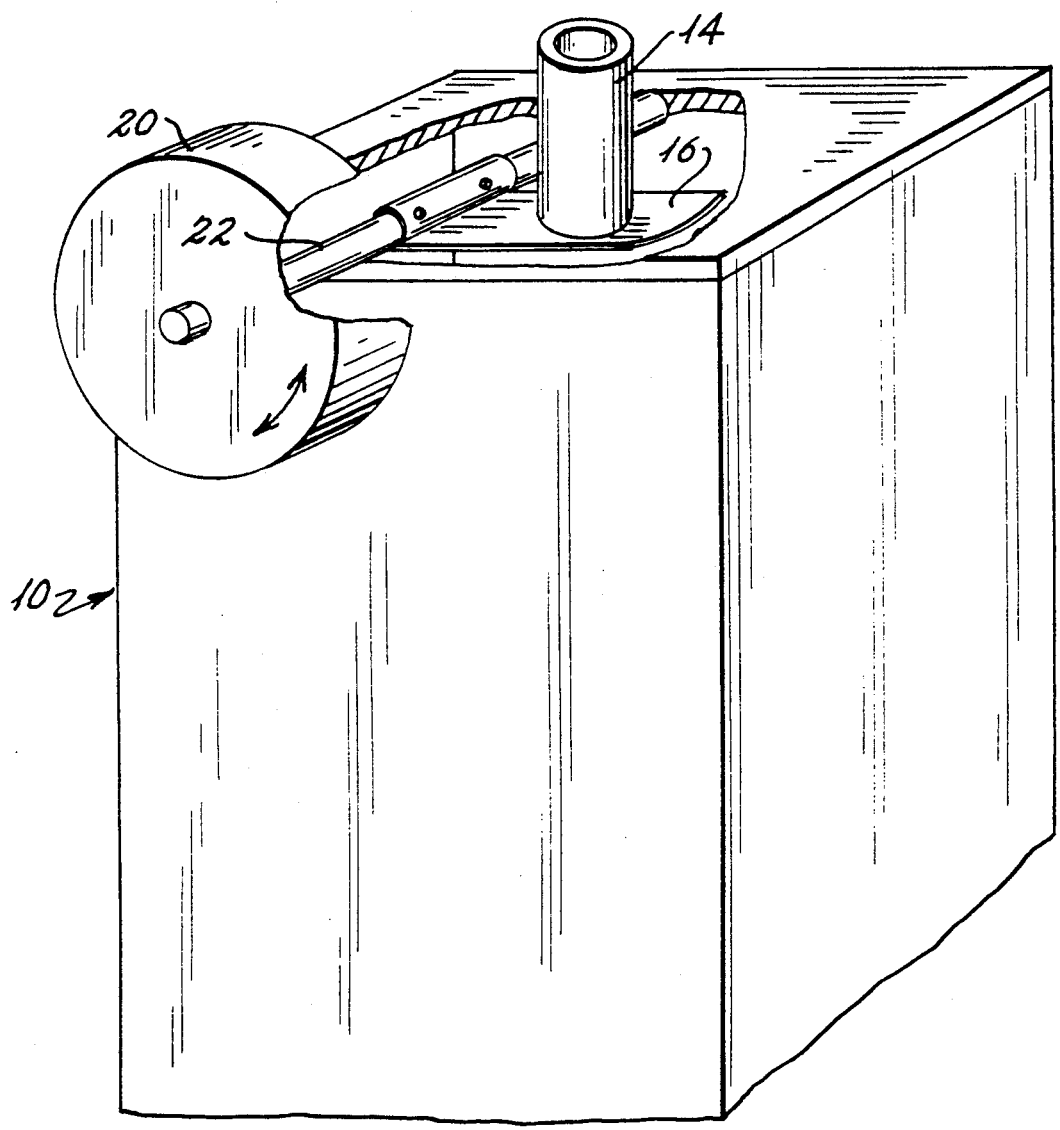
FIG. 3 is an isometric view, partially broken away, of the upper end of the test chamber in order to illustrate better the relationship between the trap door and rotary solenoid.

Referring to FIGS. 1–3, test chamber 10 is 4" square in cross-section, with a light source 32 contained in an enclosing cube 30 and a "light trap" cube 38 disposed directly opposite across the test chamber 10 from cube 30 so as to absorb all of the light from source 32 that is not scattered by the particles 2 of the sample being tested. Thus, the purpose of the light trap 38 is to remove stray light that could interfere with the measurement of the scattered light. Preferably, the light source is a miniature, incandescent lamp with a fixed aperture instead of lenses for fixing the diameter of the light beam. Such an arrangement provides a light beam that is well collimated and very uniform in intensity across the beam, without the intensity variations and other optical distortions that can occur when lenses are used as light "condensers".

The amount of stray light that is present also is minimized by the flat, orthoganolly related inner surfaces of the test chamber 10, as opposed to curved or other angularly oriented walls that tend to further reflect and scatter light so as to interfere with the measurement.

A solid state photodetector 28 in detector cube 26 is situated at a right angles to the light beam 33 emitted from light source 32 so as to receive and measure light that is scattered by the dust particles 2.

For calibration purposes, a solid state reference light source 36 such as a light emitting diode is situated within a cube directly across from the photodetector 28 for calibration of the photodetector in situ when no particles 2 are present.

Each side wall of the test chamber 10 has a vertical array of at least two light openings 12, over each of which may be positioned one of the cubes 26, 30, 34, or 38 corresponding to that wall. Thus, the cubes and devices inside of them can be repositioned along the vertical length of the test chamber 10 in order to facilitate accurate measurement of samples according to particle size. It has been found that more accurate measurement is obtainable with the larger particles when the cubes are positioned over a lower set of openings 12, with smaller particles requiring this positioning to be correspondingly higher.

Referring to FIGS. 2 and 3, the top of the test chamber 10 has a mechanism for dumping thereinto a sample of the dust or powder to be tested, including a sample cup comprising a tube 14 which extends into the chamber 10 and a trap door 16 which normally closes the bottom of tube 14 under the biasing of the internal spring of rotary solenoid 20. In a prototype of the device, the bottom of tube 14 is finely machined flat metal plate door 16 is fastened to a round metal rod 22 which is supported at each end by sealed bearings in the walls of chamber 10. The rod 22 is biased by the built-in spring of an electromechanical rotary solenoid 20 such that the rod 22 is normally biased closed in a tight sealing relation against the bottom of tube 14. When a sample contained in the tube 14 is to be dumped into the test chamber 10, the rotary solenoid is energized to pivot the trap door 16 through an arc of 95 degrees to the open position, thus allowing the sample to fall unimpeded into to test chamber 10 under the influence of gravity. An appropriate rotary solenoid is the Lucas-Ledex #S-8205-024.

Figure 6:
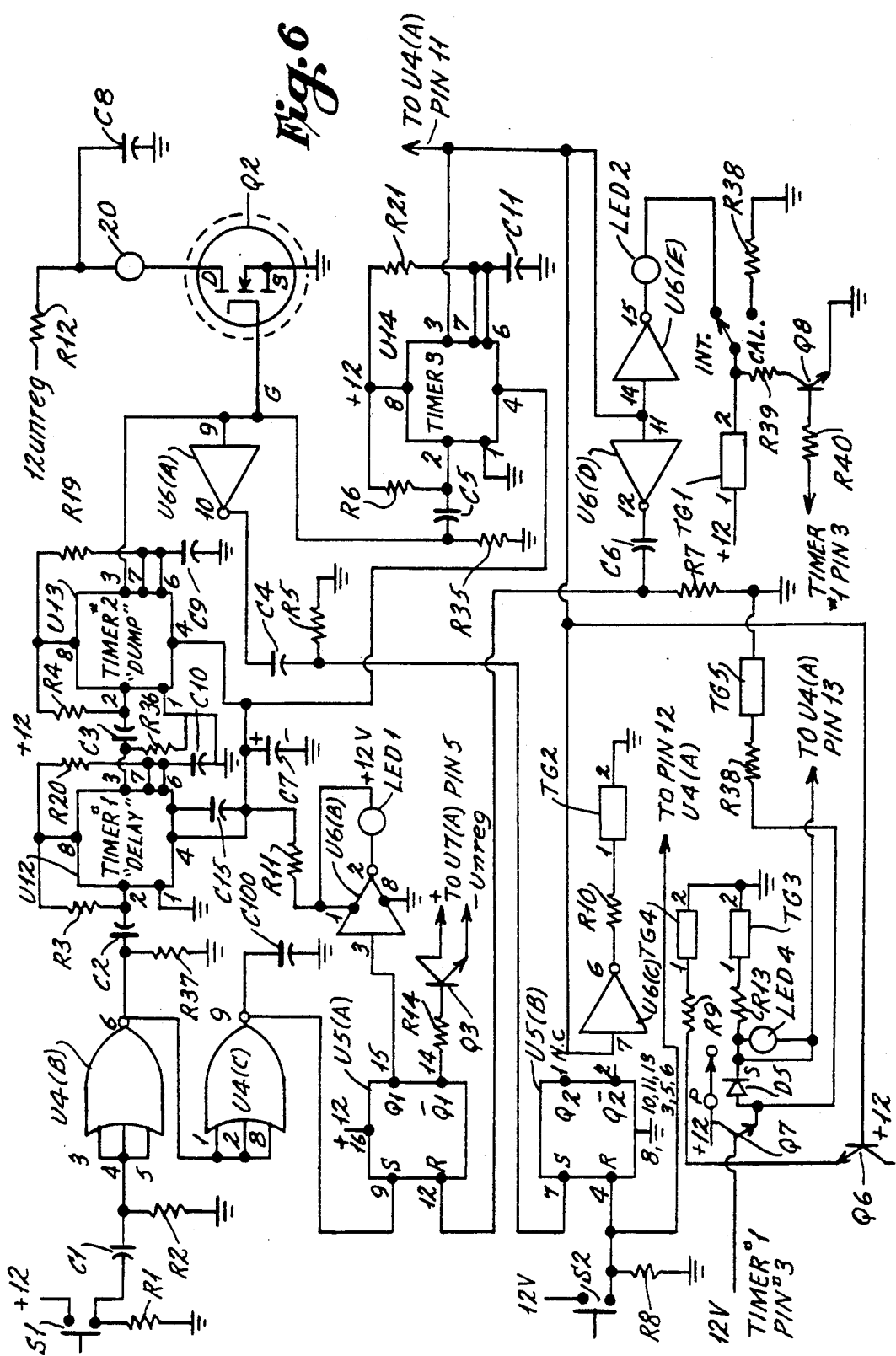
FIG. 6 is a schematic diagram of timer and logic circuits utilized in the dust measuring device of the invention.

As indicated in FIG. 8, the rotary solenoid 20 is energized for a period of 2 seconds by a "one-shot" timing circuit comprising timer #2 of FIG. 6. This timing circuit is started by an operator depressing a momentary, push button S1. The timing is presettable for a duration of 2-10 seconds and reproducible. It does not require, nor is it susceptible to intervention by, an operator.

At the bottom of the test chamber 10 is a gate valve, indicated generally at 40, for accessing a vacuum hose 42 to chamber 10 for cleaning thereof, either automatically or manually, at the end of a test or as desired by an operator.

The optical system is based upon right angle light scattering by the dust particles, and the scattered light varies directly with the amount and size of the dust particles 2. Photodetector 28 is a high speed, silicon detector, and the supporting electronics are sophisticated but simple to use as far as the operator is concerned.

Figure 5:
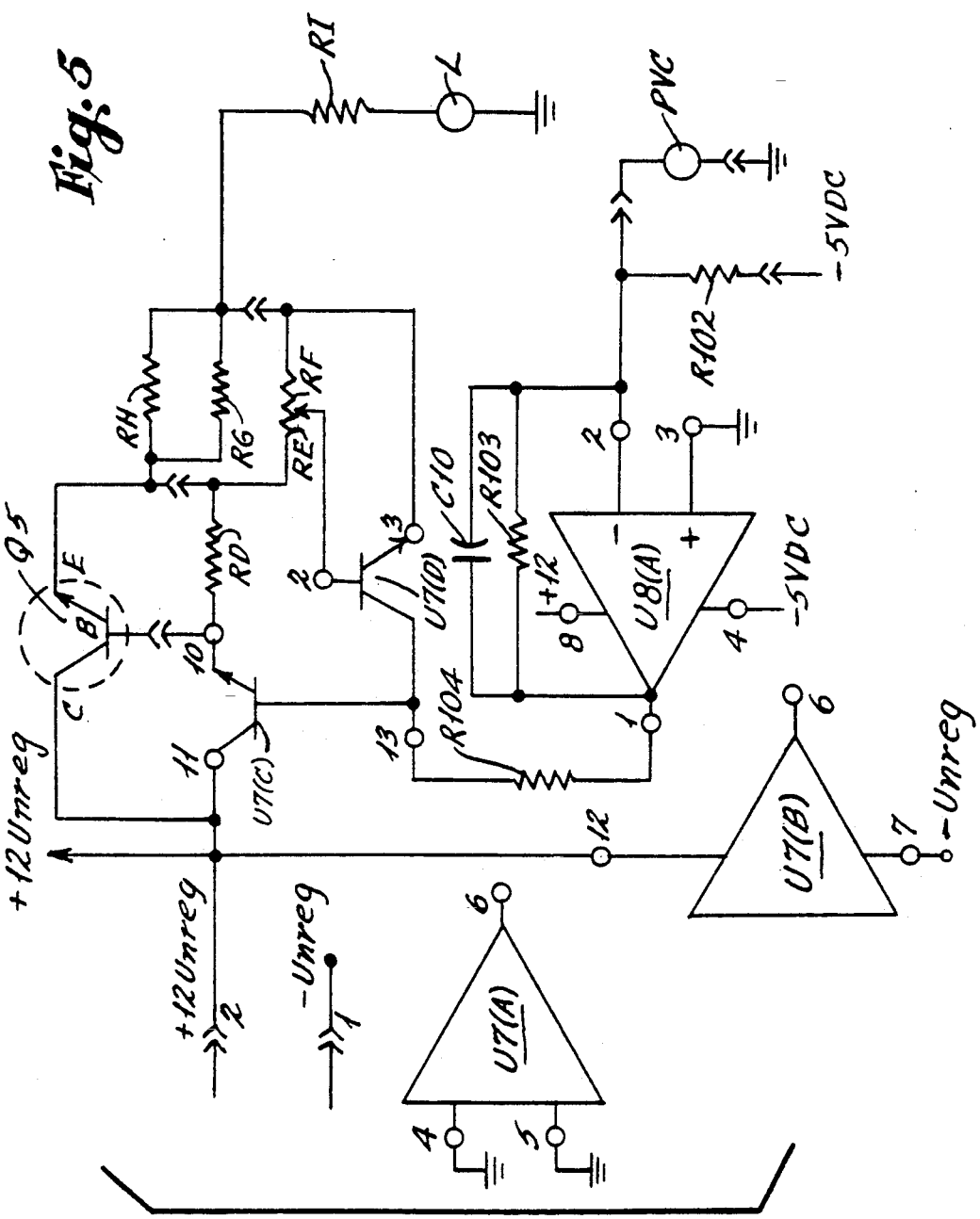
FIG. 5 is a schematic diagram of the constant light controller circuit utilized in the dust measuring device of the invention.
Figure 7:
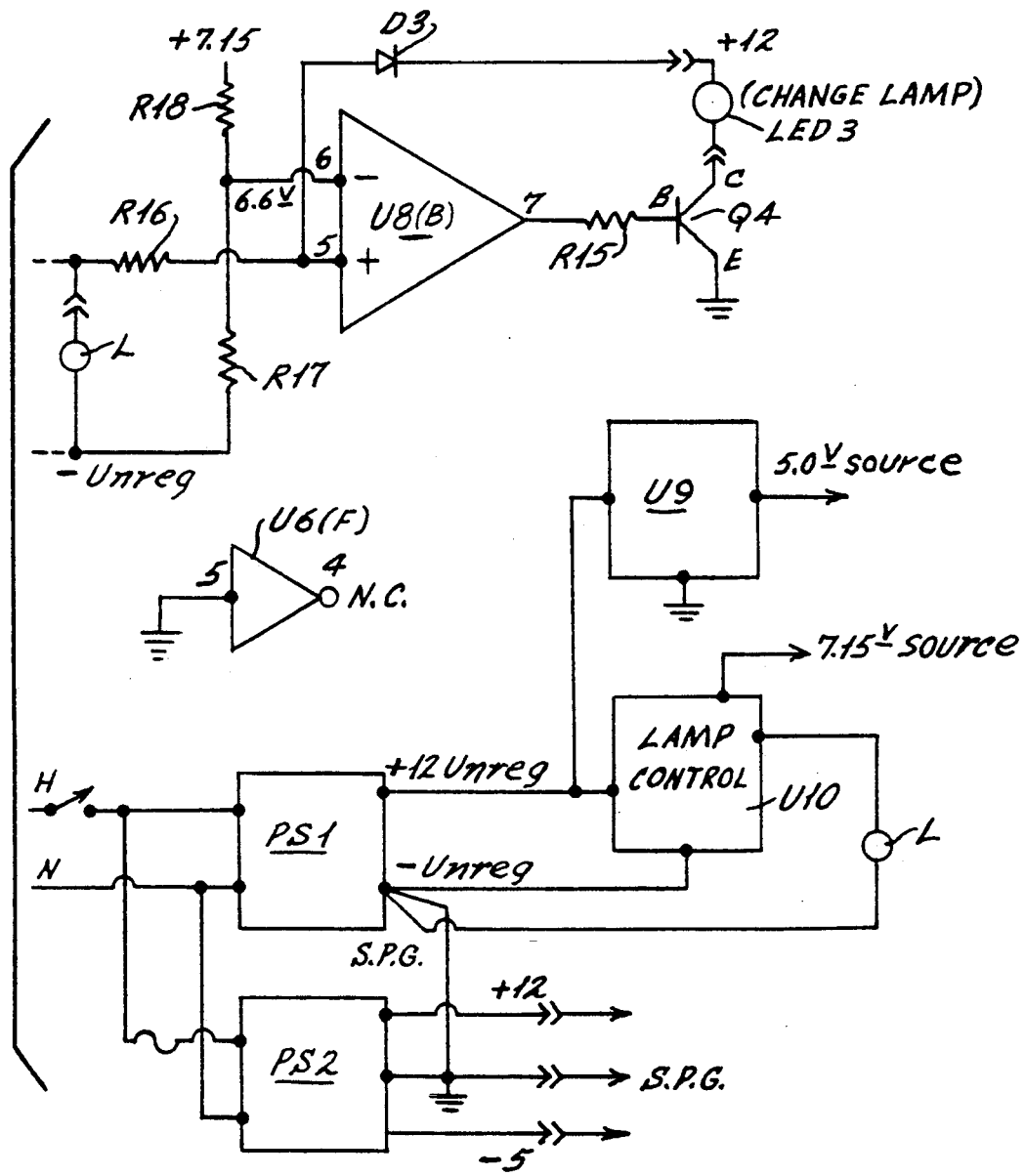
FIG. 7 is a schematic diagram of power supply and other miscellaneous circuits utilized in the dust measuring device of the invention.

The light intensity of lamp 32 is monitored continuously and controlled automatically by the circuitry of FIGS. 5 and 7 so as to be energized only for a short period of time just prior to and during a measuring cycle. Only a short warm-up period is required and, thus, there is very little performance drift caused by aging of the lamp 32. By means of LED #3 in FIG. 7, the unit indicates to the operator the need to change the lamp 32.

Supporting electronic circuits provide the necessary timing signals and other control signals for the apparatus to perform the testing and output the "characteristic number" automatically, without human intervention other than depressing the "start" push button. The majority of the circuitry and functions of FIGS. 5–7 generally may be considered to be prior art. However, at the heart of the inventive device is the multifunction circuit illustrated in schematic form in FIG. 4a and in block form in FIG. 4b, and a detailed description thereof follows.

MULTIFUNCTION CKT BLOCK 50

Figure 4A:
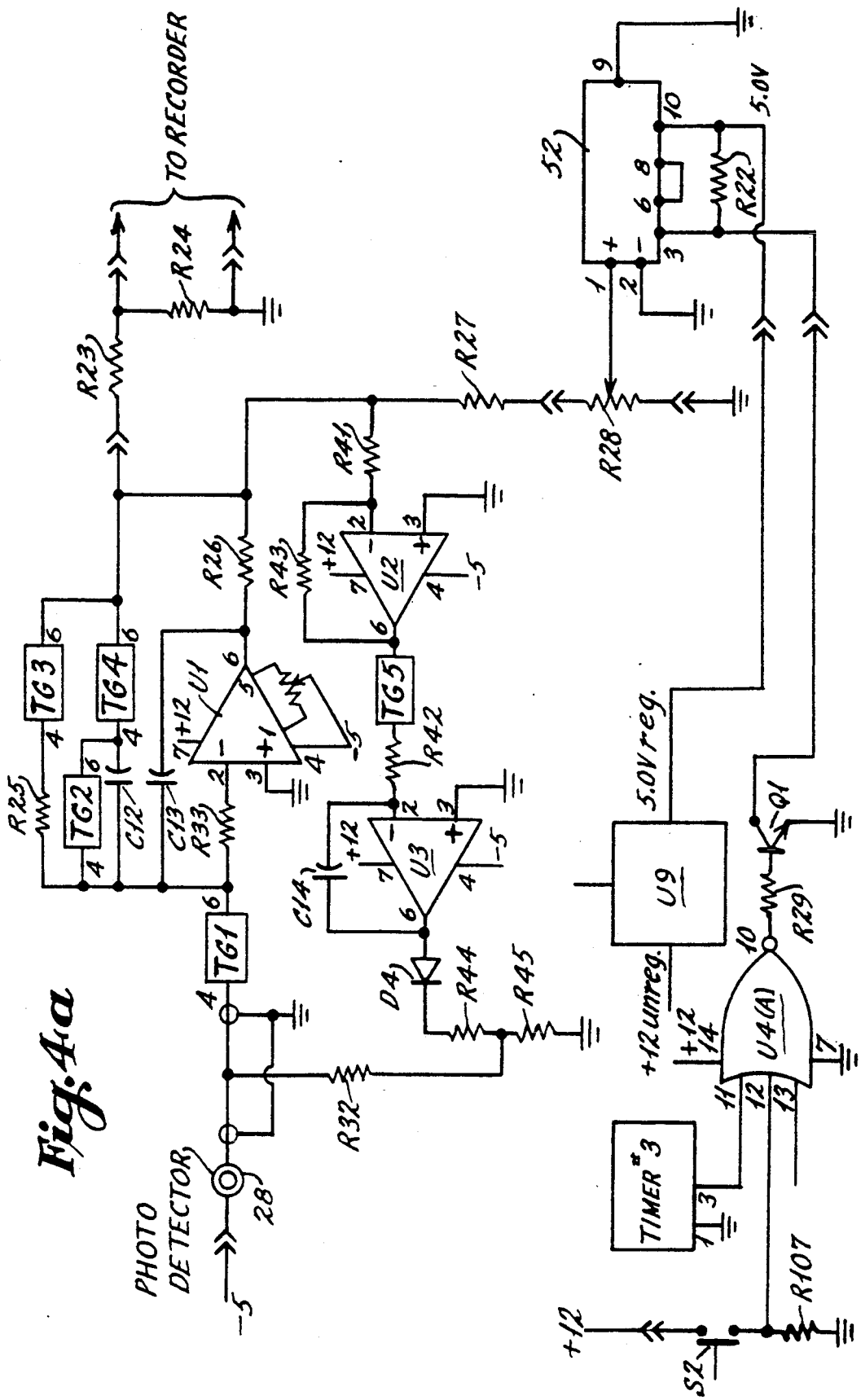
FIG. 4a is a schematic diagram of integrating and autozeroing circuit of the dust measuring device of the invention.
Figure 4B:
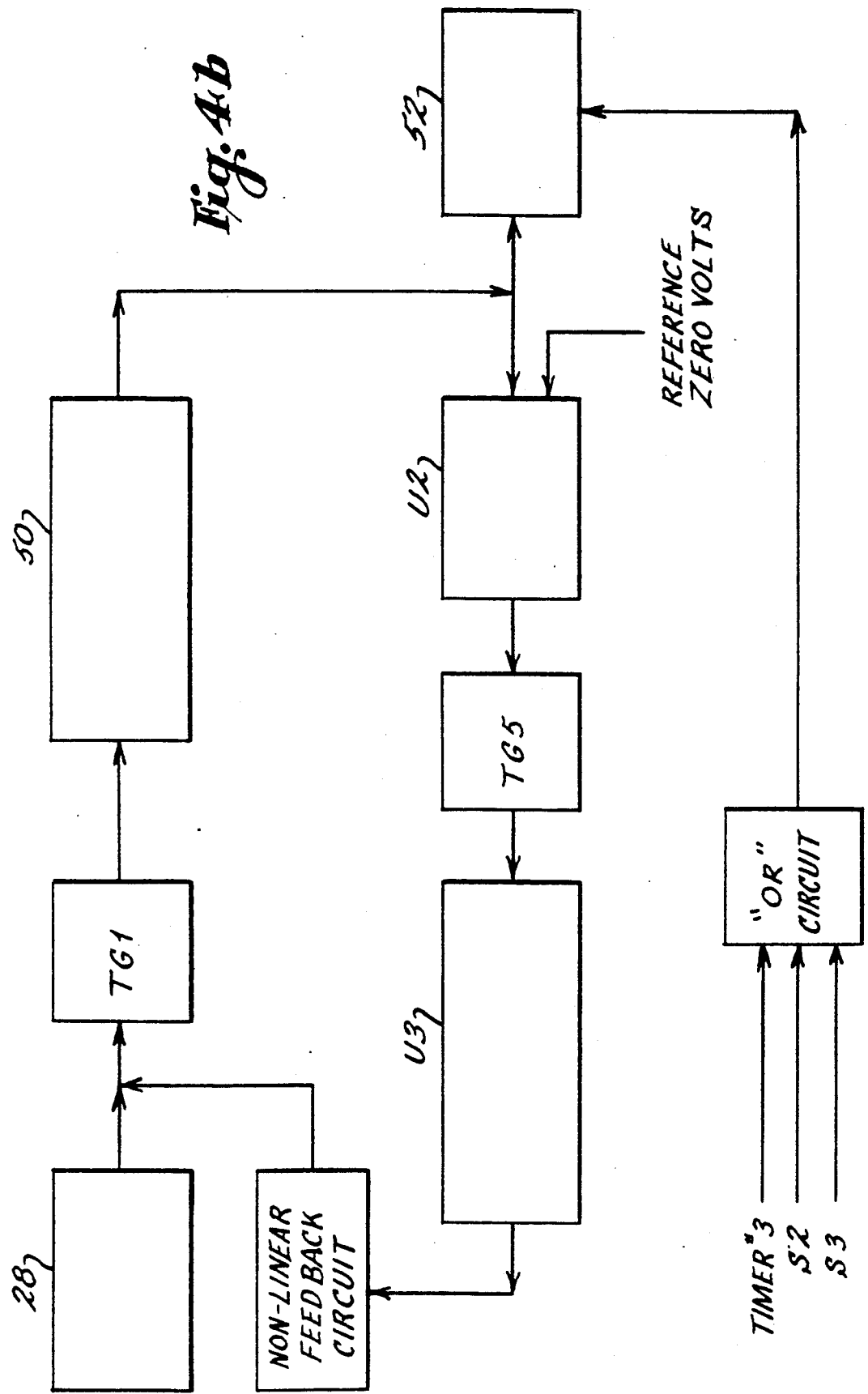

Referring to FIGS. 4a and 4b, the input to multifunction circuit block 50 is current from the photodetector 28 via transmission gate TG1, which: (i) during a normal measurement, is proportional to the light intensity received by the photodetector 28 from the incandescent bulb 32 which reflects off of the material 2 being tested and impinges upon the photodetector 28, or (ii) during calibration of the device is proportional to the light intensity received by the photodetector 28 directly from a reference light 36 when no material to be tested is in the chamber 10.

The cornerstone of this multifunction circuit block 50 is a high quality, high input resistance, operational amplifier U1 (type 515) which, with its supporting circuitry and according to control signals which are provided to transmission gates TG1, TG2, TG3, and TG4, becomes: (i) a noninverting, unity gain amplifier used for automatic zero adjustment [along with U2 as part of the autozeroing circuit] (ii) a current integrator device with variable resistor Ra serving as a means for adjusting the initial value of the time integral to zero, or (iii) a means for reversing polarity of the photo current from photodetector 28 in order to adjust the integrator output to zero as required (when used in combination with U2 and U3 during autozeroing).

An output voltage from block 50 is fed to an automatically controlled digital panel meter 52.

The output also is fed to a constant gain inverting amplifier U2 which is part of the auto-zeroing circuit. U2 compares the output voltage from the "multifunction" block 50 against a zero volt reference, multiplies any difference resulting from the comparison by a constant multiplier number (in this example, by −39) and sends the result to TG5. When TG5 is turned "on" during the automatic zeroing period, any voltage between it and resistor R42 represents an amplified error of block 50 relative to zero volts. For accurate, reproducible results, this error voltage must be zero and, thus, the auto-zeroing is required.

A high input resistance operational amplifier U3, in conjunction with resistor R42 and capacitor C14, forms a voltage integrator with a long RC time constant. Thus, an output voltage of this integrating opam U3 changes far slower than an output voltage of block 50 so as to provide a correcting input signal to block 50 without block 50 losing overall control.

Diode D4 and resistors R44, R45 and R32 form a nonlinear, current feedback circuit at the output of the voltage integrator U3 for further enhancing the performance of the voltage integrator. The feedback circuit responds differently depending on the polarity and magnitude of the voltage on the output terminal of U3. Utilizing the non-linear action of a diode in the manner illustrated results in a non-linear voltage divider network by which faster zeroing of block 50 is obtained.

For instance, when the output voltage of U3 is positive and large, say +10 volts, then the effect of the diode D4 (across which there is a relatively small voltage drop of about 0.6 volts) on the voltage divider is negligible, and the voltage at the intersection of R44, R45 and R32 is determined by the voltage dividing action of R44 and R45.

However, when this output voltage is about +0.6 volts and lower, the diode D4 has a prominent effect on the voltage divider because the voltage across the diode varies logarithmically with the current therethrough. When this output voltage is negative, the diode D4 is reverse biased and no longer conducts in the forward direction and presents a very high back resistance. With this high value of back resistance, the diode D4 provides total control of the voltage at the interconnection of R44, R45, and R32, resulting in a markedly different control action when the voltage is negative.

Because of these control actions, the current through R32 varies in a non-linear manner that is determined by the magnitude and polarity of the amplified "error" signal during the zeroing process. Thus, an electronically stable, reproducible zero adjustment is obtained by a timed electronic sequence, without human intervention.

Of the following three different electrical outputs from the multifunction circuit block 50, only one may be used at any one time: (1) to a recorder as indicated across R24 of FIG.; this output is proportional to the instantaneous amount of scattered light and is recordable versus time on an optional, conventional strip chart recorder as in the above-referenced Lorenz publication, (2) to the built-in digital panel meter 52 (FIGS. 4a and 4b) which displays a single number which is characteristic of the dust sample measured so that this "characteristic number" can be used to rate numerically the different samples being evaluated; this normal operation output corresponds to the time integral of the scattered light or the area under the curve of the strip chart output and requires no digital computer to reduce the data to useable form; this output provides for rating of the various samples numerically in simple terms such as a ratio of the meter readings, (3) to the digital paner meter 52 when calibrating the device against the stable, solid-state reference light source 26 in order to insure close agreement between different units of the inventive device for the same sample.

Thus, the objects set forth above, among those made apparent from the preceding description, are efficiently attained and, since certain changes may be made in the construction set forth without departing from the scope of the invention, it is intended that all matter contained in the above description or shown in the accompanying drawings shall be interpreted as illustrative and not in a limiting sense.

The following claims are intended to cover all of the generic and specific features of the invention herein described and all statements of the scope of the invention which, as a matter of language, might be said to fall therebetween.

Now that the invention has been described, we claim:

1. In a method of evaluating dustiness of a sample of a substance by dropping said sample past a test light source of a test chamber and detecting an amount of light from said test light source which is received by a photodetector of said test chamber, wherein said amount of light received by said photodetector is affected by an interference between said sample and said light directed from said test light source, the improvement comprising the steps of:
   a. integrating an output from said photodetector in response to, and over a period of time of, said detecting;
   b. outputting a single characteristic number in response to said integrating, said number being characteristic of said dustiness of said sample;
   c. providing a reference light source for said test chamber;
   d. eliminating light to said test chamber from said test light source;
   e. providing light to said test chamber from said reference light source only; and
   f. calibrating said apparatus during use of said reference light source.

2. The improvement as in claim 1, and further comprising the step of:
   performing said calibrating without interference of a substance sample with light from said reference light source during said calibrating.

3. In an apparatus for evaluating dustiness of a substance sample, said apparatus having a test chamber, a test light source for projecting light into said test chamber, and a photodetector for receiving and detecting an amount of light from said test light source according to an interference between said sample and said light directed from said test light source, the improvement comprising:
   a. means for receiving an output from said photodetector in response to said detecting;
   b. means for integrating said photodetector output over a period of time of said detecting;
   c. means for outputting a single characteristic number in response to said integrating, said number being characteristic of said dustiness of said sample;
   d. reference light source means for projecting a reference light into said test chamber during a calibration mode of operation of said apparatus;
   e. means for eliminating light to said test chamber from said test light source and projecting light into said test chamber from said reference light source only during said calibration mode; and
   f. means for calibrating said apparatus by use of said reference light source during said calibration mode.

4. The improvement as in claim 3, and further comprising:

means for zeroing said integrating means automatically in preparation for evaluating each said sample.

5. The improvement as in claim 4, wherein said zeroing means comprises:
a non-linear feedback circuit means for zeroing of said integrating means; and
means for enabling said feed back circuit automatically only during a delay period prior to dropping each said sample into said test chamber.

6. The improvement as in claim 11, wherein said test light source has a light projecting central axis and said photodetector has a light receiving central axis, and further comprising:
means for orienting said light projecting and light receiving central axes generally coplanarly and generally perpendicularly to each other in order to receive, at said photodetector, light from said test light source which is reflected from said sample during said evaluating.

* * * * *